United States Patent [19]
Schmelzeisen et al.

[11] Patent Number: 5,947,970
[45] Date of Patent: Sep. 7, 1999

[54] ENDOSCOPIC BONE PLATE POSITIONING DEVICE

[75] Inventors: Rainer Schmelzeisen, Freiburg; Udo Wichmann, Harsum; Uwe Schaardt, Hanover, all of Germany

[73] Assignee: Synthes (USA), Paoli, Pa.

[21] Appl. No.: 09/064,874

[22] Filed: Apr. 23, 1998

[30] Foreign Application Priority Data

Apr. 23, 1997 [DE] Germany ........................ 197 17 977

[51] Int. Cl.⁶ .................................................. A61B 17/56
[52] U.S. Cl. .............................. 606/70; 600/104; 606/96
[58] Field of Search .................................. 606/69, 70, 71, 606/99, 100, 101, 96; 600/104

[56] References Cited

U.S. PATENT DOCUMENTS

| | | | |
|---|---|---|---|
| D. 320,414 | 10/1991 | Morgan .................................... | D20/22 |
| 3,856,016 | 12/1974 | Davis ....................................... | 128/325 |
| 4,471,766 | 9/1984 | Terayama ................................. | 128/6 |
| 4,854,302 | 8/1989 | Allred, III ................................ | 128/6 |
| 4,923,471 | 5/1990 | Morgan .................................... | 623/16 |
| 4,959,065 | 9/1990 | Arnett et al. ............................. | 606/69 |
| 4,994,910 | 2/1991 | Williams .................................. | 358/98 |
| 5,199,417 | 4/1993 | Muller et al. ............................. | 128/6 |
| 5,334,150 | 8/1994 | Kaali ........................................ | 604/164 |
| 5,373,840 | 12/1994 | Knighton ................................. | 128/4 |
| 5,377,668 | 1/1995 | Ehmsen et al. .......................... | 128/4 |
| 5,423,826 | 6/1995 | Coates et al. ............................ | 606/96 |
| 5,558,669 | 9/1996 | Reynard ................................... | 606/15 |
| 5,569,160 | 10/1996 | Sauer et al. .............................. | 600/114 |
| 5,641,287 | 6/1997 | Gittleman ................................. | 433/75 |
| 5,658,236 | 8/1997 | Sauer et al. .............................. | 600/114 |
| 5,667,475 | 9/1997 | Laser et al. .............................. | 600/127 |
| 5,667,478 | 9/1997 | McFarlin et al. ....................... | 600/182 |
| 5,690,631 | 11/1997 | Duncan et al. .......................... | 606/69 |
| 5,700,267 | 12/1997 | Urbanski .................................. | 606/86 |
| 5,700,275 | 12/1997 | Bell et al. ................................ | 606/208 |
| 5,702,463 | 12/1997 | Pothier et al. ........................... | 623/20 |
| 5,725,523 | 3/1998 | Mueller .................................... | 606/15 |
| 5,732,992 | 3/1998 | Mauldin .................................. | 294/119.1 |
| 5,755,721 | 5/1998 | Hearn ....................................... | 606/69 |

*Primary Examiner*—Michael Buiz
*Attorney, Agent, or Firm*—Pennie & Edmonds LLP

[57] ABSTRACT

A device for implanting a bone plate is disclosed. The device includes an endoscope attachment element having a body member sized to receive at least a portion of an endoscope and a bone plate holder having one end sized to receive at least a portion of a bone plate. The bone plate holder is operatively associated with the body member of the attachment element to move the bone plate holder between a first retracted position and a second implanting position. In preferred embodiments, the attachment element includes a guide track for providing sliding movement of the holder and the track has a plurality of catches for grasping a locking button on the holder to retain the holder in the implanting position. The device preferably includes a locking member having a connecting tube operatively associated with the bone plate to guide and enable fastening operations through an aperture in the body member of the attachment element so that the bone plate can be secured to bone.

12 Claims, 4 Drawing Sheets

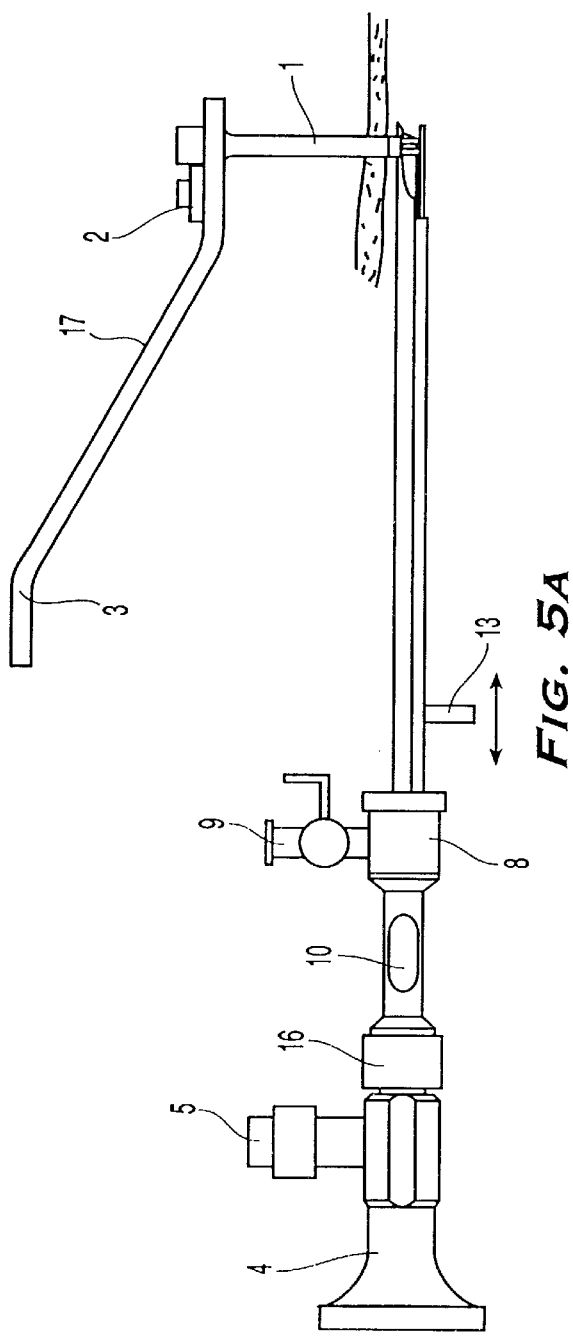
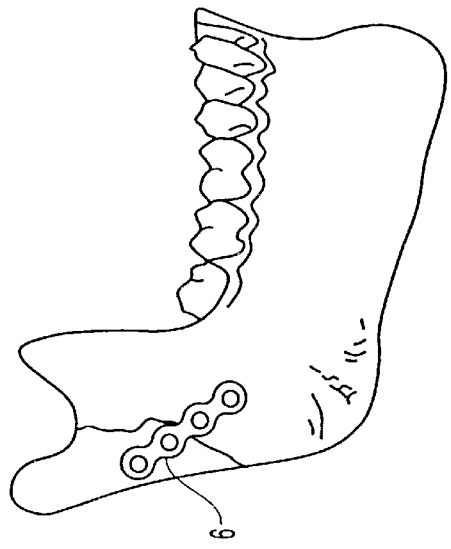
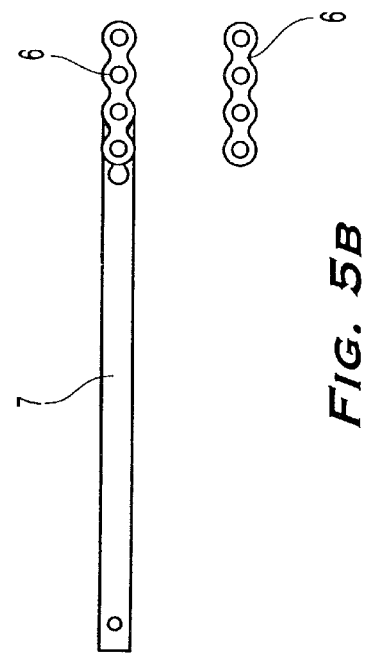
FIG. 5A
FIG. 5B
FIG. 6

ENDOSCOPIC BONE PLATE POSITIONING DEVICE

FIELD OF THE INVENTION

The present invention relates to a method for the stabilization of bone fractures and in particular to an endoscopic bone plate positioning device for use in such a procedure.

BACKGROUND OF THE INVENTION

Most mandibular fractures must be treated operatively. Often it is not possible to fix the fracture from the oral mucous membrane. For this reason, these types of fractures have been treated from a skin incision made in front of the ear.

One possible serious complication in accessing the mandible from the cheek is damage to the facial nerve which divides into its branches in the parotid salivary gland, i.e., the immediate vicinity of the skin incision. Additionally, access from the exterior carries with it the possibility of aesthetically unappealing scarring.

The risk of the above complications can be reduced by minimizing the surgical trauma associated with fixing a fracture. Endoscopic procedures are minimally invasive procedures which stabilize the fracture using a small incision, and hence decrease the surgical trauma associated with fixing a fracture. However, because of the small incision, it is difficult to implant the bone plate used to fix the fracture.

Thus, there exists a need for an improved device for implanting a bone plate to conduct such procedures while minimizing complications.

SUMMARY OF THE INVENTION

The present invention relates to a device for implanting a bone plate including an endoscope attachment element having proximal and distal ends and a body member configured and dimensioned to receive at least a portion of an endoscope, and a bone plate holder having one end which is configured and dimensioned to hold at least a portion of the bone plate. The bone plate holder is operatively associated with the body member of the endoscope attachment element to move the bone plate holder between a first retracted position and a second implanting position.

In one embodiment, the endoscope attachment element includes a guide track positioned adjacent the body member for receiving the bone plate holder and for providing sliding movement of the bone plate holder between the first and second positions. Preferably, the guide track includes a plurality of bone plate holder positioning catches and the bone plate holder includes a locking button for engaging one of the catches to retain the bone plate holder in the second implanting position.

In another embodiment, the body member of the endoscope attachment element has a distal end which includes a raspatory having an aperture therein, wherein the aperture aligns with the end of the bone plate holder when the bone plate holder is retained in the second implanting position.

The endoscope attachment element can have an integrated irrigation and suction system as well as a handle for manipulation.

The device preferably further includes a locking member which has a connecting tube operatively associated with the bone plate to guide and enable fastening operations through the bone plate screw holes. In order to secure the connecting tube to the endoscope attachment element once the bone plate has been properly positioned, an end of the connecting tube can have a first securing element and the endoscope attachment element can have a second securing element.

BRIEF DESCRIPTION OF THE DRAWINGS

FIG. 5A is a side view of the device according to the present invention in use;

FIG. 5B is a top view illustrating how the slider holds the bone plate; and

FIG. 6 is a schematic showing a mandibular fracture fixed by a bone plate.

DESCRIPTION OF THE PREFERRED EMBODIMENTS

Figure 1A:
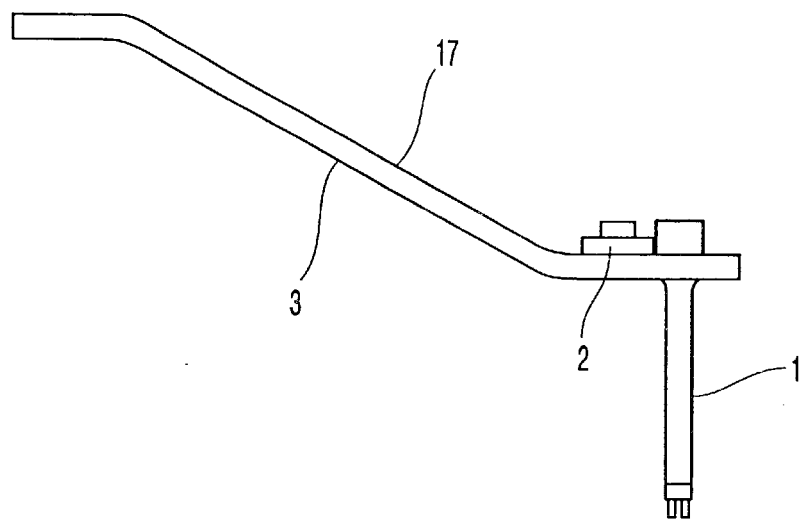
FIG. 1A is a side view of a locking piece according to the present invention.
Figure 1B:
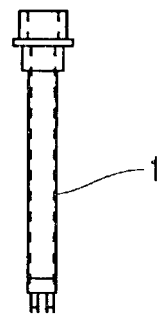
FIG. 1B is side view of a connecting tube according to the present invention.
Figure 1C:
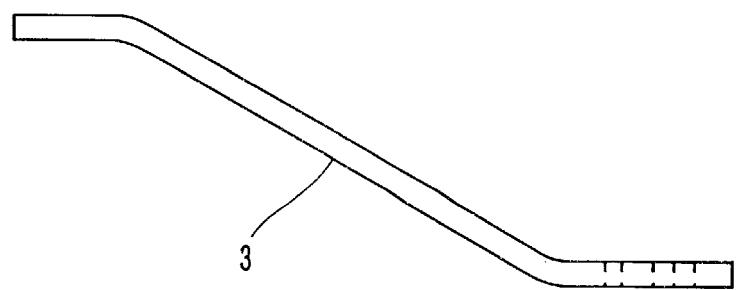
FIG. 1C is a side view of a grip according to the present invention.
Figure 3:
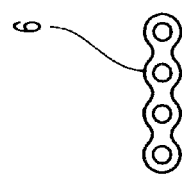
FIG. 3 is a top view of a bone plate that can be used with the present invention.

FIG. 1A shows a locking member 17, one of the components of the device according to the present invention. Locking member 17 includes a connecting tube 1 attached to a grip 3 by a shim 2. Connecting tube 1 can be a trocar. As shown in FIG. 1B, connecting tube 1 has a hollow interior through which a drill bit, screwdriver, screw, or any fastener can be inserted to attach a bone plate 6 (FIG. 3) to bone. Alternatively, connecting tube 1 is equipped with a drill bit.

Figure 2:
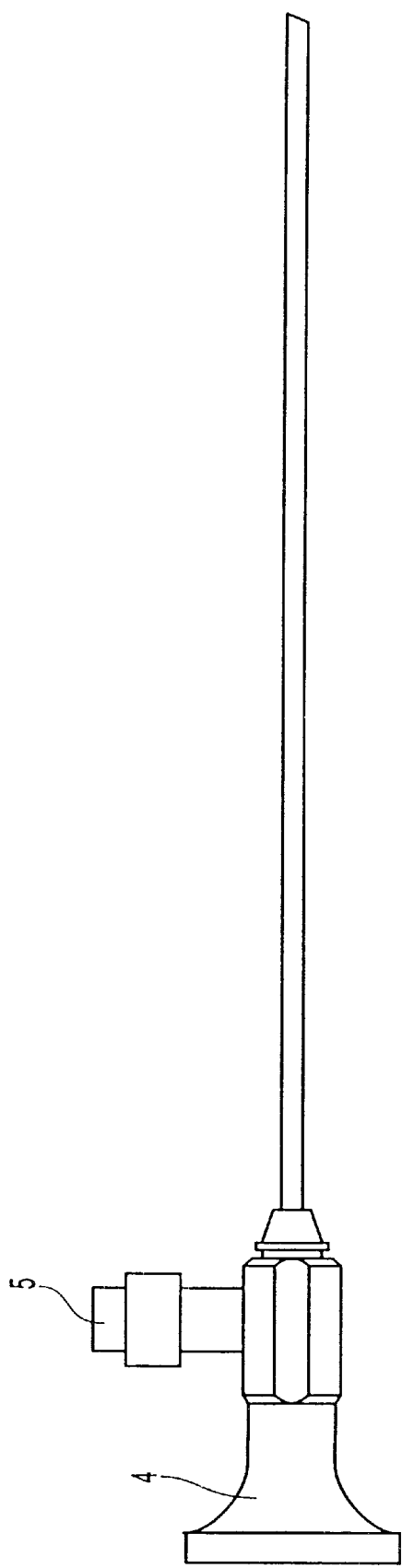
FIG. 2 is a side view of an endoscope that can be used with the present invention.
Figure 4A:
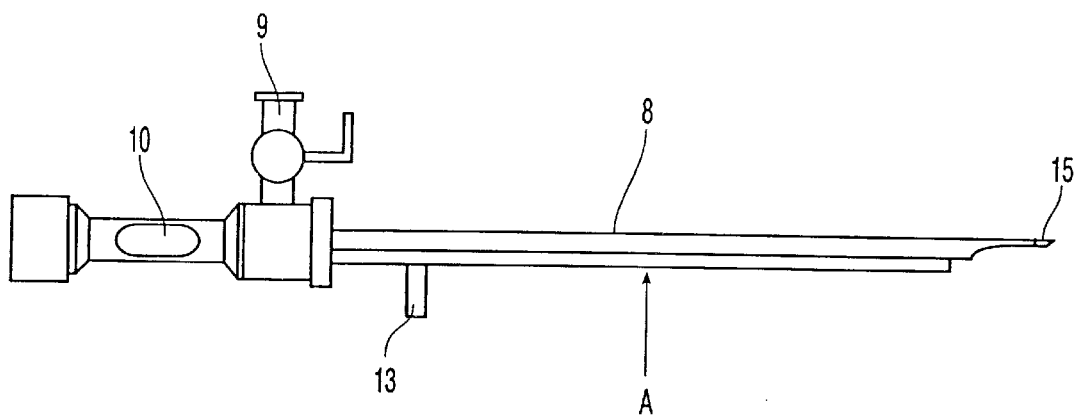
FIG. 4A is a side view an endoscope attachment element according to the present invention.
Figure 4B:
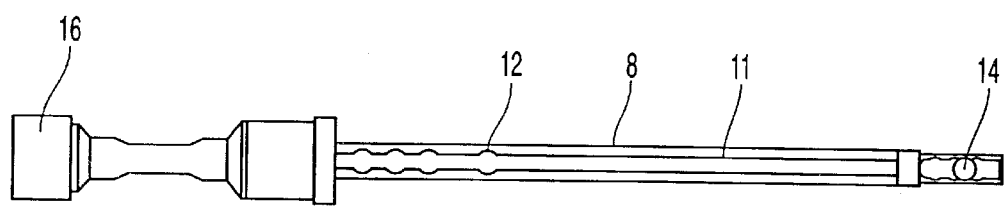
FIG. 4B is a bottom view (in the direction of arrow A in FIG. 4A) of the endoscope attachment element.
Figure 4C:
FIG. 4C is a top view of a slider of the endoscope attachment element.

FIGS. 4A and 4B show an endoscope attachment element 8, another component of the device according to the present invention. Attachment element 8 has a distal end 15 and a proximal end 16 through which at least a portion of endoscope 4 (FIG. 2) is inserted into a body member 18. A handle 10 provides a means for the user to manipulate attachment element 8. Attachment element 8 also includes a bone plate holder 7 having one end configured and dimensioned to hold at least a portion of bone plate 6. Bone plate holder 7 is operatively associated with body member 18 of attachment element 8 to move bone plate holder 7 between a first retracted position and a second implanting position. Distal end 15 is preferably shaped like a raspatory.

A guide track 11 is positioned adjacent body member 18 and extends along the length of attachment element 8. Bone plate holder 7 is inserted in guide track 11 and can move along guide track 11 to change the position of bone plate 6 so that one of the screw holes of bone plate 6 aligns with an aperture 14 on attachment element 8. In order to prevent movement of bone plate holder 7 along guide track 11, one of the catches 12 on guide track 11 grasps a locking button 13 located on bone plate holder 7.

The use of the device according to the present invention will be illustrated using the fixation of a mandibular fracture as an example. After surgical preparation which is standard for an endoscopic procedure, the surgeon makes a first incision at the mandibular angle. The surgeon first reduces the fracture using a surgical tool introduced through the first incision. Endoscopic attachment element 8, having a portion of endoscope 4 extending through body member 18 and bone plate holder 7 holding bone plate 6 is introduced through the first incision. Using the light from an illumination means 5, the fracture and surround area can be viewed using endoscope 4. As attachment element 8 has an optional integrated irrigation and suction system 9, any impediments to visualization can be removed. Once bone plate 6 is in the desired position, bone plate holder 7 is moved along guide track 11 until at least one screw hole of bone plate 6 aligns with aperture 14. In order to prevent loss of this alignment, locking button 13 is fixed to one of the catches 12.

After positioning of bone plate 6, the surgeon makes a second incision directly above the fracture. Connecting tube 1 of locking member 3 is introduced through this second incision and is securely connected to distal end 15 of attachment element 8. One way of achieving this secure connection is by providing an end of connecting tube 1 with a first securing element and distal end 15 of attachment element 8 with a second securing element such that the first and second securing elements cooperate to attach connecting tube 1 to attachment element 8. A drill bit is introduced through connecting tube 1 to create a hole through which a screw can be used to fix bone plate 6 to the bone. After all screws have been inserted and attachment element 8 and locking member 17 have been detached from each other and removed from the incisions, both incisions are closed.

While it is apparent that the illustrative embodiments of the invention herein disclosed fulfil the objectives stated above, it will be appreciated that numerous modifications and other embodiments may be devised by those skilled in the art. Therefore, it will be understood that the appended claims are intended to cover all such modifications and embodiments which come within the spirit and scope of the present invention.

What is claimed is:

1. A device for implanting a bone plate comprising:

an endoscope attachment element having proximal and distal ends and a body member configured and dimensioned to receive at least a portion of an endoscope, and a bone plate holder having one end which is configured and dimensioned to hold at least a portion of the bone plate;

wherein the bone plate holder is operatively associated with the body member of the endoscope attachment element to move the bone plate holder between a first retracted position and a second implanting position.

2. The device of claim 1, wherein the endoscope attachment element includes a guide track positioned adjacent the body member for receiving the bone plate holder and for providing sliding movement of the bone plate holder between the first and second positions.

3. The device of claim 2, wherein the guide track includes a plurality of bone plate holder positioning catches therealong, and the bone plate holder includes a locking button for engaging one of the catches to retain the bone plate holder in the second implanting position.

4. The device of claim 3, wherein the body member of the endoscope attachment element has a distal end having an aperture therein, wherein the aperture aligns with the end of the bone plate holder when the bone plate holder is retained in the second implanting position.

5. The device of claim 1, wherein the endoscope attachment element includes an integrated irrigation and suction system for introducing a fluid to clear debris from the distal end of the endoscope attachment element.

6. The device of claim 1, further comprising a handle for manipulating the endoscope attachment element.

7. The device of claim 1, further comprising an endoscope placed at least partially within the body member of the endoscope attachment element for viewing the distal end of the endoscope attachment element.

8. The device of claim 1, further comprising a bone plate having at least one screw hole and being retained in position by the bone plate holder.

9. The device of claim 8, further comprising a locking member which includes a connecting tube operatively associated with the bone plate to guide and enable fastening operations through the at least one bone plate screw hole.

10. The device of claim 9, wherein the locking member includes a grip for manipulation thereof.

11. The device of claim 10, wherein the connecting tube is mounted to the grip with a shim.

12. The device of claim 10, wherein the connecting tube includes a first securing element and the distal end of the endoscope attachment element has a second securing element, with the first and second securing elements cooperating to securely connect the connecting tube to the endoscope attachment element.

* * * * *